United States Patent [19]

Bitter et al.

[11] 4,250,335
[45] Feb. 10, 1981

[54] PREPARATION OF 2,3,5-TRIMETHYLHYDROQUINONE

[75] Inventors: Johan G. A. Bitter; Rudolf J. Maas; Jacobus H. Scheerman, all of Amsterdam, Netherlands

[73] Assignee: Shell Oil Company, Houston, Tex.

[21] Appl. No.: 769,810

[22] Filed: Feb. 17, 1977

[30] Foreign Application Priority Data

Feb. 19, 1976 [GB] United Kingdom ............ 6606/76

[51] Int. Cl.³ ............................................ C07C 37/00
[52] U.S. Cl. ................................................. 568/771
[58] Field of Search .......... 260/621 H, 621 R, 621 G, 260/625; 252/463; 568/772, 771

[56] References Cited

U.S. PATENT DOCUMENTS

| 2,229,573 | 1/1941 | Darmstadt | 260/621 H |
| 2,259,936 | 10/1941 | Darmstadt | 260/621 H |
| 3,658,853 | 4/1972 | Schuster et al. | 260/396 R |
| 3,839,468 | 10/1974 | Tamai et al. | 260/621 H |
| 3,927,045 | 12/1975 | Michelet | 260/621 H |

Primary Examiner—Werren B. Lone

[57] ABSTRACT

An improved process is described for the preparation of 2,3,5-trimethylhydroquinone by catalytically oxidizing a trimethylphenol selected from the class consisting of 2,3,5-trimethylphenol, 2,3,6-trimethylphenol and mixtures thereof with oxygen in the presence of a cobalt chelate catalyst complex in a dimethylformamide solvent to form 2,3,5-trimethyl-p-benzoquinone which is subsequently hydrogenated to 2,3,5-trimethylhydroquinone by reaction with hydrogen in the presence of a noble metal catalyst. In this improved process, the 2,3,5-trimethyl-p-benzoquinone-containing reaction mixture from catalytic oxidation is contacted with di-n-butyl ether and water to form a di-n-butyl ether phase containing the 2,3,5-trimethyl-p-benzoquinone, a precipitate comprising the cobalt catalyst and an aqueous phase containing the dimethylformamide solvent, said di-n-butyl ether phase being subsequently separated from the precipitate and aqueous phase and passed to the catalytic hydrogenation reaction where the di-n-butyl ether functions as the reaction solvent.

6 Claims, 1 Drawing Figure

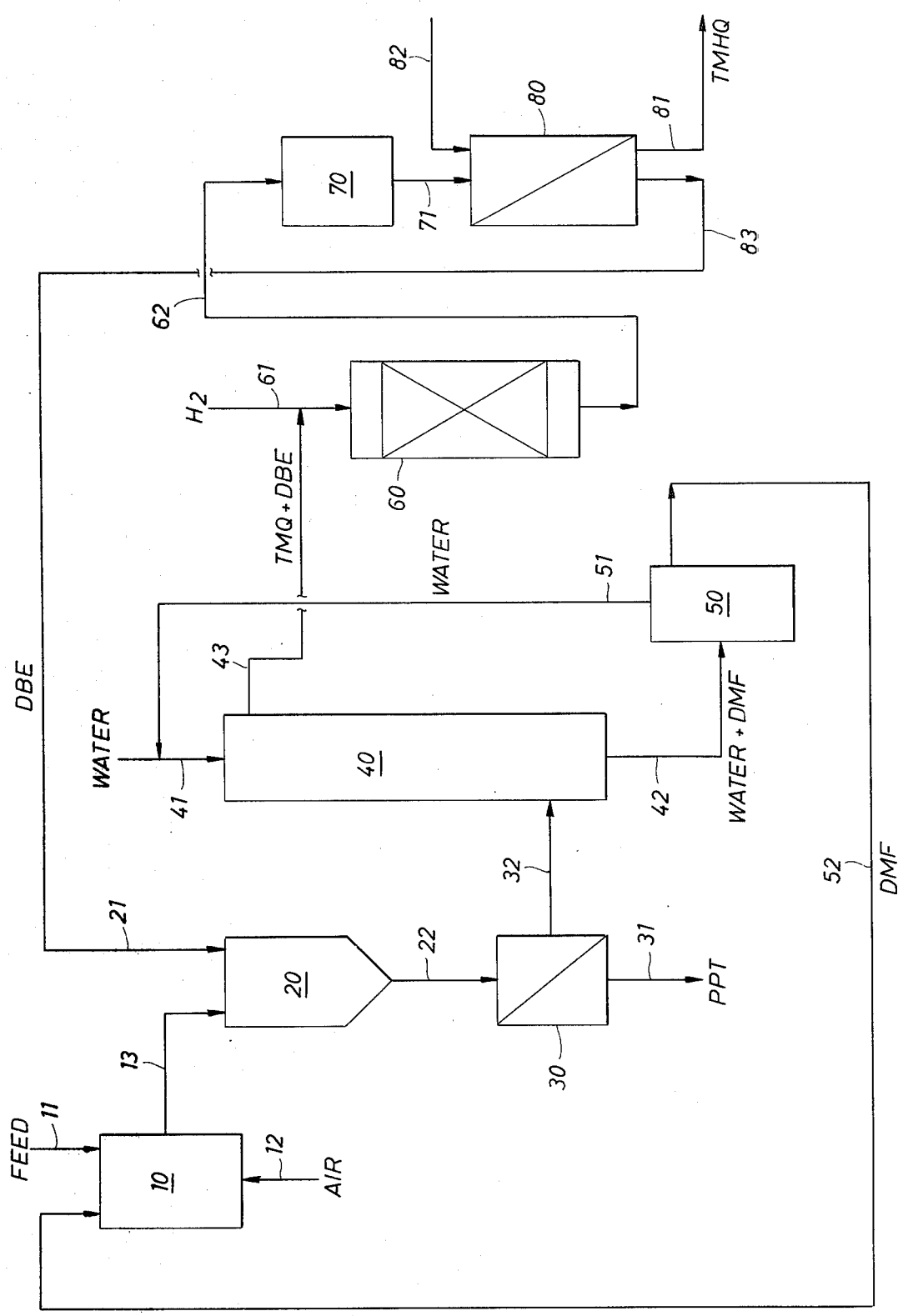

PREPARATION OF 2,3,5-TRIMETHYLHYDROQUINONE

BACKGROUND OF THE INVENTION

This invention relates to a process for the preparation of 2,3,5-trimethylhydroquinone (hereinafter referred to as TMHQ) by the catalytic oxidation of 2,3,5-and/or 2,3,6-trimethylphenol to 2,3,5-trimethyl-p-benzoquinone (hereinafter referred to as TMQ) followed by catalytic hydrogenation of the TMQ.

TMHQ has a rather broad utility in commerce, including application as a antioxidant and UV stabilizer in addition to its use as a starting material or intermediate in preparing pharmaceuticals. In particular, TMHQ finds special application as an intermediate for the production of alpha-tocopheral which is itself used in the production of vitamin E.

It is known that TMHQ can be prepared from 2,3,6-trimethylphenol by sequential oxidation and hydrogenation as described above. However, in general these two reactions require the use of different catalysts and usually the use of different solvents. Thus, from U.S. Pat. No. 3,658,852 it is known that 2,3,6-trimethylphenol may be oxidized to TMQ with oxygen in the presence of a cobalt chelate complex such as bis(-salicylideneethylenediimine)cobalt(II) as catalyst and a substituted amide, for example dimethylformamide, as solvent. In contrast, U.S. Pat. No. 3,839,468 teaches a process for catalytic hydrogenation of TMQ to TMHQ which employs a palladium catalyst and an aliphatic ketone solvent. This second patent also discusses other, apparently less successful, prior art attempts to conduct the catalytic hydrogenation reaction in solvents such as alcohols, hydrocarbons, ethers and carboxylic acids and gives comparative examples using solvent such as tertiary butanol and diisopropyl ether.

While the preparative scheme described above may be suitable for laboratory scale synthesis of TMHQ it suffers certain disadvantages when applied on a commercial scale. Specifically the change from one catalyst/solvent system to another such system can give rise to problems when these two reactions are to be carried out successively on a large scale. That is, both the catalyst and solvent must be removed completely from the reaction product of the initial oxidation reaction before the catalyst and solvent for the second reaction can be added to the system. Thus, unless considerable care and associated expenses is involved in the initial catalyst and solvent removal, the initial reaction product will likely be contaminated with residual catalyst and/or solvent which may adversely effect the subsequent hydrogenation reaction. The present invention provides a method whereby the two reactions may be conveniently carried out in sequence to afford high yields of TMHQ.

SUMMARY OF THE INVENTION

It has now been found that the above mentioned sequential catalytic oxidation and hydrogenation reactions in the preparation of TMHQ from 2,3,5-and/or 2,3,6-trimethylphenol can be readily carried out with the associated separation of catalyst and solvent from the TMQ product of the first reaction, if the oxidation reaction mixture is mixed with di-n-butyl ether and water in amounts sufficient to form a di-n-butyl ether phase containing TMQ, a precipitate comprising the oxidation catalyst and an aqueous phase containing the oxidation reaction solvent. In this improved process, which takes advantage of the apparently unique properties of the di-n-butyl ether as an extractant for TMQ in the presence of water, the di-n-butyl ether phase containing the TMQ is easily separated from the solvent and catalyst of the oxidation reaction and passed to the hydrogenation reaction where the di-n-butyl ether functions as an excellent reaction solvent.

Accordingly, the instant invention provides an improved process for the preparation of TMHQ by (a) catalytic oxidation of a trimethylphenol starting material selected from the class consisting of 2,3,5-trimethylphenol, 2,3,6-trimethylphenol and mixtures thereof by reaction with oxygen in the presence of a cobalt chelate complex in a dimethyl formamide solvent to afford TMQ followed by (b) catalytic hydrogenation of the TMQ thus formed by reaction with hydrogen in the presence of a noble metal catalyst. This improved process is characterized in that the TMQ containing reaction mixture from step (a) is mixed with di-n-butyl ether and water to form a di-n-butyl ether phase containing TMQ, a precipitate comprising the cobalt catalyst and an aqueous phase containing the dimethylformamide reaction solvent with the di-n-butyl ether phase being separated from the precipitate and aqueous phase and subject to the catalytic hydrogenation according to reaction step (b), said di-n-butyl ether functioning as the reaction solvent.

DESCRIPTION OF THE PREFERRED EMBODIMENTS

The cobalt complex used in the oxidation step (a) is preferably an iminato complex of formula:

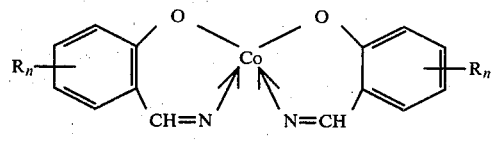

A wherein A is an ethylene or phenylene group; each R is a hydrogen or halogen atom, a nitro or hydroxy group, or an alkyl group of 1 to 4 carbon atoms; and n is an integer from 1 to 4. A particularly preferred complex is N,N'-ethylenebis(salicylideneiminato)cobalt(II) also referred to as Salcomine.

The amount of trimethylphenol starting material used is preferably 5 to 50% by weight based on the dimethyl formamide, and the cobalt chelate catalyst used is preferably 1 to 15% by weight based on the trimethylphenol. The temperature of the oxidation may be from 20° to 100° C., preferably 50° to 80°, and the oxygen pressure may be from 1 to 14 atm.

The treatment of the TMQ-containing dimethylformamide solution from step (a) with di-n-butyl ether and water is preferably carried out sequentially. The addition of di-n-butyl ether results in the formation of a single liquid phase and a precipitate comprising the catalyst and usually some polymeric material formed as by-products. The amount of di-n-butyl ether added is preferably 70 to 90% by weight based on the total weight of dimethylformamide+TMQ. It is also possible to use a lower amount of di-n-butyl ether if the water formed during the oxidation step is first removed from the dimethylformamide solution. The temperature at which the di-n-butyl ether is added to the dimethylformamide solution may be from 20° to 100° C. and is preferably from 50° to 80° C.

The liquid phase and precipitate may then be separated, for example, by filtration or decantation, and the liquid phase washed with water to remove the dimethylformamide. The amount of water used is preferably the minimum necessary to remove substantially all the dimethylformamide from the di-n-butyl ether and is preferably from 0.2 to 3 times the weight of dimethylformamide present. The solubility of water in di-n-butyl ether is low and consequently only a small amount of water remains in the di-n-butyl ether phase after the separation of the aqueous phase. This small amount of water has no adverse effect on the subsequent hydrogenation step (b) and its complete removal is not necessary.

The catalyst used in step (b) is preferably palladium which may be supported on an inert carrier, for example, aluminium oxide. The temperature of the hydrogenation may be from 20° to 100° C. and the pressure of hydrogen may be from 1 to 15 atm. Since the reaction is exothermic, the temperature of the reaction mixture will, in the absence of external cooling, rise during the reaction. The TMHQ may be recovered from the reaction mixture by conventional means, for example, by filtering or centrifuging off the catalyst and cooling the filtrate to effect crystallization of the TMHQ product.

The process of the invention will now be described further by reference to the accompanying drawing which shows a typical process flow scheme for a preferred embodiment recording to the invention.

The oxidation step is carried out in the reactor 10, into which a feed consisting of the trimethylphenol (TMP), cobalt chelate catalyst and dimethylformamide (DMF) solvent is introduced via line 11. The mixture is stirred at 70° C. while air added via line 12 is passed through it. On completion of the oxidation the mixture is passed by line 13 to a separation vessel 20, in which di-n-butyl ether (DBE) is added by line 21 to bring about precipitation of the catalyst and any polymeric material. The slurry formed is passed via line 22 to a filter 30 where the precipitate is filtered off, said precipitate being removed via line 31. The filtrate is then passed via line 32 to a scrubber column 40 where it is washed with water introduced via line 41. The aqueous phase which contains the DMF is removed as a bottoms product by line 42 and fractionally distilled in the distillation apparatus 50 to give water which is recycled via lines 51 and 41 to the column 40 and DMF which is recycled by line 52 to the reactor 1. The DBE phase from the column 40, which contains the TMQ, is passed by line 43 to a second reactor 60 in which it is catalytically reduced with molecular hydrogen introduced via line 61 over a bed of the palladium catalyst. After the reduction, the DBE solution is removed via line 52 and cooled to 20° C. in the crystallization vessel 70. The cooled slurry is passed by line 71 to the filter 80 where the crystallized TMHQ is then filtered off and removed via line 81. If desired, the TMHQ may be washed with a suitable low-boiling liquid introduced via line 82 to remove any traces of DME and/or water and then dried. The filtrate from the crystallization contains about 1.0%w of TMHQ in the DBE. This filtrate may be recycled via line 83 without further treatment to the separation vessel 20. In this way the ultimate recovery of TMHQ may approach 100%.

The invention is illustrated further in the following Examples.

EXAMPLES

In all the Examples the oxidation and hydrogenation steps were carried out as follows:

(a) Oxidation 2,3,5-Trimethylphenol and N,N'-ethylenebis(salicylideneiminato)cobalt(II) were dissolved in N,N-dimethylformamide (DMF). The solution was stirred vigorously at 70° C. while oxygen at atmospheric pressure was passed through the solution.

(b) Hydrogenation 2,3,5-Trimethyl-p-benzoquinone (TMQ) in di-n-butyl ether (DBE) and gaseous hydrogen at a pressure of 3 atm abs (molar ratio $H_2$:TMQ=1.25:1) were passed over a catalyst consisting of 2%w palladium on a gamma alumina carrier. The temperature of the solution was initially 40° C. but rose during the reaction to about 100° C.

EXAMPLE I

The solution from the oxidation (a) contained 1 parts by weight (pbw) of TMQ+DMF, the weight ratio TMQ:DMF being 1:3, and 1 mol of water per mol of TMQ. This solution was treated with 7.6 pbw of DBE at 70° C. A single liquid phase was obtained together with a precipitate containing catalyst and polymeric by-product. The precipitate could be easily filtered off. The liquid phase was then washed with water (3×0.67 pbw). The DBE solution which contained 3.23%w TMQ was then hydrogenated as described in (b). The solution was then cooled to 20° C. to bring about crystallization of the TMHQ which was filtered off. The yield of TMHQ was 69%w based on TMQ starting material.

EXAMPLES II and III

These Examples were carried out in a similar manner to that described in Example I except that the ratio TMQ:DMF and the amount of DBE added were varied. In each case a single liquid phase was obtained on addition of the DBE and the precipitate could be easily filtered off. The results are summarized in the Table below.

TABLE

| Example | Weight Ratio TMQ:DMF | DBR pbw | TMQ/DBE Soln. %w | Yield TMHQ %w |
|---|---|---|---|---|
| 2 | 1:2 | 5.67 | 5.57 | 82 |
| 3 | 1:1.27 | 3.55 | 13.62 | 91 |

COMPARATIVE EXPERIMENT

In this experiment a solution having a TMQ:DMF ratio of 1:1 was used. This solution has been stripped of the water formed during the oxidation in an attempt to assist the formation of a single liquid phase. The procedure of Example I was followed except that di-isopropyl ether (4.55 pbw) was used in place of DBE. Under these conditions two liquid phases were obtained and the precipitate could not be satisfactorily separated.

On the other hand a 1:1 TMQ/DMF solution requires only 2.8 pbw of DBE for the formation of a single liquid phase and a completely separable precipitate.

What is claimed is:

1. In the process for the preparation of 2,3,5-trimethylhydroquinone by (a) catalytic oxidation of a trimethylphenol starting material selected from the class consisting of 2,3,5-trimethylphenol, 2,3,6-trimethylphenol and mixtures thereof by reaction with oxygen in the presence of a cobalt chelate complex in a dimethylformamide solvent to afford 2,3,5-trimethyl-p-benzoquinone followed by (b) catalytic hydrogenation of the 2,3,5-trimethyl-p-benzoquinone thus formed by reaction with hydrogen in the presence of a noble metal catalyst, the improvement which comprises; (1) mixing the 2,3,5-trimethyl-p-benzoquinone containing reaction mixture from step (a) with di-n-butyl ether and water to form a di-n-butyl ether phase containing 2,3,5-trimethyl-p-benzoquinone, a precipitate comprising the cobalt catalyst and an aqueous phase containing the dimethylformamide reaction solvent, (2) separating the di-n-butyl ether phase from the precipitate and aqueous phase, and (3) subjecting the separated di-n-butyl ether phase to catalytic hydrogenation according to reaction step (b), said di-n-butyl ether functioning as the reaction solvent.

2. The process according to claim 1, wherein the reaction mixture from step (a) is first mixed with di-n-butyl ether to form a single liquid phase and a precipitate comprising the cobalt catalyst, the catalyst precipitate is separated from the liquid phase and the separated liquid phase is mixed with water to form a two-phase liquid mixture made up of a di-n-butyl ether phase containing 2,3,5-trimethyl-p-benzoquinone and an aqueous phase containing the dimethylformamide solvent, said di-n-butyl ether phase being subsequently separated from the aqueous phase and subject to catalytic hydrogenation according to reaction step (b).

3. The process according to claim 2, wherein the amount of di-n-butyl ether used is 70 to 90% by weight based on the total weight of dimethylformamide plus 2,3,5-trimethyl-p-benzoquinone.

4. The process according to claim 3, wherein the di-n-butyl ether is added at a temperature of 20° to 100° C.

5. The process according to claim 4, wherein the amount of water used is from 0.2 to 3 times the weight of dimethylformamide present in the reaction mixture from step (a).

6. The process according to claim 1, wherein the catalytic hydrogenation step (b) is carried out using a palladium catalyst support on an aluminum oxide carrier.

* * * * *